United States Patent
Köhler et al.

(10) Patent No.: US 6,937,888 B2
(45) Date of Patent: Aug. 30, 2005

(54) SIGNAL EVALUATION METHOD FOR DETECTING QRS COMPLEXES IN ELECTROCARDIOGRAM SIGNALS

(75) Inventors: Bert-Uwe Köhler, Berlin (DE); Reinhold Orglmeister, Berlin (DE)

(73) Assignee: Biotronik GmbH & Co. KG, Berlin (DE)

( * ) Notice: Subject to any disclaimer, the term of this patent is extended or adjusted under 35 U.S.C. 154(b) by 516 days.

(21) Appl. No.: 10/067,391

(22) Filed: Feb. 7, 2002

(65) Prior Publication Data

US 2002/0133085 A1 Sep. 19, 2002

(30) Foreign Application Priority Data

Feb. 7, 2001 (DE) ........................... 101 05 431

(51) Int. Cl.[7] .................................................. A61B 5/04
(52) U.S. Cl. ..................................................... 600/521
(58) Field of Search ............................... 600/509, 508, 600/521

(56) References Cited

U.S. PATENT DOCUMENTS

| | | |
|---|---|---|
| 3,552,386 A | 1/1971 | Horth |
| 5,701,907 A | 12/1997 | Klammer |
| 5,836,982 A | 11/1998 | Mühlenberg et al. |

FOREIGN PATENT DOCUMENTS

DE 196 26 353 A1 1/1998

OTHER PUBLICATIONS

Jiapu Pan et al. "A Real–Time QRS Detection Algorithm", IEEE Transactions on Biomedical Engineering, vol. BME–32, No. 3, Mar. 1985.

G. M. Friesen et al. "A Comparison of the Noise Sensitivity of Nine QRS Detection Alogrithms", IEEE Transactions on Biomedical Engineering, IEEE Inc. New York, US, Bd. 37, Nr. 1, 1990, Seiten 85–98.

*Primary Examiner*—Mark Bockelman
(74) *Attorney, Agent, or Firm*—Browdy and Neimark, P.L.L.C.

(57) ABSTRACT

A signal evaluation method for detecting QRS complexes in electrocardiogram (ECG) signals comprises the following steps:

sampling of the ECG signal (4) and conversion into discrete signal values (x(n)) in chronological order;

comparing the signal values ($x_f(n)$, $x_{fq}(n)$) to a threshold function (K(n)) adaptively determined therefrom;

determining a frequency number (D(n)) within a defined segment of the consecutive signal values, by which signal values ($x_f(n)$, $x_{fq}(n)$) preferably fall short of the threshold function (K(n));

comparing the determined frequency number (D(n)) to a defined threshold (Θ), wherein an undershoot of the threshold (Θ) is significant for apresence of a QRS complex (5, 6, 7) in the defined segment of the ECG signal (4).

9 Claims, 2 Drawing Sheets

SIGNAL EVALUATION METHOD FOR DETECTING QRS COMPLEXES IN ELECTROCARDIOGRAM SIGNALS

BACKGROUND OF THE INVENTION

1. Field of the Invention

The invention relates to a signal evaluation method for detecting QRS complexes in electrocardiogram (ECG and IEGM) signals.

2. Background Art

Regarding the background of the invention, it can be stated that the automatic analysis of ECG signals is playing an increasingly larger role in perfecting the functionality of cardiac pacemakers and defibrillators. Newer models of implantable cardiac devices of this type accordingly also offer the capability to perform an ECG analysis. The detection of QRS complexes and R spikes in ECG signals plays an extremely important role in this context. This significance results from the many and diverse applications for the information concerning the time of occurrence of the QRS complex, for example when examining the heart rate variability, in the classification and data compression, and as the base signal for secondary applications. QRS complexes and R spikes that are not detected at all or detected incorrectly pose problems with respect to the efficiency of the processing and analysis phases following the detection.

A wide overview of known signal evaluation methods for detecting QRS complexes in ECG signals can be found in the technical essay by Friesen et al. "A Comparison of the Noise Sensitivity on Nine QRS Detection Algorithms" in IEEE Transaction on Biomedical Engineering, Vol. 37, No. 1, January 1990, pages 85–98. The signal evaluation algorithms presented there are based throughout on an evaluation of the amplitude, the first derivation of the signal, as well as its second derivation. For the presented algorithms, the essay distinguishes between those that perform an analysis of the amplitude and the first derivation, those that analyze only the first derivation, and those that take into consideration the first and second derivation. To summarize briefly, all algorithms check whether the given signal parameter exceeds or falls short of any predetermined thresholds, after which, if such an event occurs, the occurrence of additional defined events is checked based on a predefined pattern, and if certain criteria are fulfilled, the conclusion is drawn that a QRS complex is present.

Another aspect in the signal evaluation for detecting QRS complexes needs to be taken into account when methods of this type are implemented in implanted cardiac devices. In view of the natural limitations of these devices regarding their energy supply and computing capacity, it is important that the detection of QRS complexes can be performed with the simplest possible algorithms with the fewest possible mathematical operations on the basis of whole numbers instead of real numbers.

Signal processing methods from the fields of linear and non-linear filtering, wavelet transformation, artificial neural networks and genetic algorithms have also been applied in the QRS detection. With large signal-noise distances and non-pathological signals, i.e., when good signal conditions are present, these evaluation methods produce reliable results. When no such conditions were present, the efficiency of the evaluation processes could drop drastically, which, of course, is not acceptable with regard to the reliable operation of a pacemaker.

Finally, QRS detection on the basis of zero crossing counts is known from Applicant's prior German patent application no. 100 11 733.3 which has however been published subsequently. It comprises the following process steps:

sampling of the signal and conversion into discrete signal values in chronological order;

high-pass filtering of the sampled signal values;

determining the sign of each signal value;

continuous checking of the signs of consecutive signal values for the presence of a zero crossing between two consecutive signal values;

determining the number of zero crossings in a defined segment of the consecutive signal values; and comparing the determined number of zero crossings to a defined threshold value, with a lower deviation from the threshold value signifying the presence of a QRS complex in the defined segment of the signal curve.

So as to in this case obtain a significantly high number of zero crossings in the range outside the QRS complexes, a high-frequency overlay signal of low amplitude as compared to the amplitude of the QRS complex is added to the high- or band-pass filtered and squared ECG signal.

Of course, this way of proceeding conflicts with the demand, explained at the outset, for simplest possible algorithms.

SUMMARY OF THE INVENTION

Based on the described problems, the invention has as its object to present a signal evaluation method for detecting QRS complexes in ECG signals that can be used with a comparatively low computing capacity and also with problematic signal conditions while producing reliable detection results.

This object is met with the process steps according to the invention as follows:

sampling of the ECG signal and conversion into discrete signal values of chronological order;

comparing the signal values to a threshold function adaptively determined therefrom;

determining a frequency number within a defined segment of the consecutive signal values, by which preferably the absolute values of the signal values fall short of the threshold function;

comparing the determined frequency number to a defined threshold, wherein an undershoot of the threshold is significant for the presence of a QRS complex in the defined segment of the ECG signal.

The core element of the inventive method is the application of a threshold comparison and a subsequent frequency count, based on utilizing the morphology of the QRS complex. The QRS complex in the ECG signal is characterized by a relatively high-amplitude oscillation that markedly guides the signal curve away from the regularly noisy and offset-actuated zero line of the electrocardiogram. The frequency of this short oscillation lies within a range in which other signal components, such as the P and T wave, exert only minor influence and can be removed preferably by pre-filtering—for example high-pass or band-pass filtering. After suppression of these low-frequency signal components, signal fluctuations result around the zero line, due to higher-frequency noise, that dominate the ECG signal in the range where no QRS complex occurs. The QRS complex then appears in this signal context as a slow, high-amplitude oscillation of only short duration that significantly leads away from the zero line of the ECG signal. If the signal values are compared to a threshold function representative of the signal noise, the amounts of the signal values outside the QRS complex mostly undershoot this threshold function. In this regard, the frequency number is great by which the amounts of the signal values undershoot the threshold function. In the range of the QRS complex, the amounts of the signal values significantly exceed the threshold function. Consequently, a small frequency number of undershoots of the threshold is found in the course of the QRS complex. So the QRS complex can be selected by comparison of the determined frequency number with a defined threshold value. An undershoot of the threshold value signifies the overshoot of the threshold function that is typical of the QRS complex.

The method, according to the invention, of QRS complex detection has proven robust with regard to noise interference and easy to implement with respect to the computing technology. In this regard, it is particularly suitable for implementation in the real time analysis of ECG signal morphologies in cardiac pacemakers.

The previously mentioned high-pass filtering is performed preferably with a low pass frequency of 18 Hz. In this way, the low-frequency components, such as the P and T waves as well as a base line drift, can be suppressed. Furthermore, the QRS complex thus becomes the signal component with the lowest frequency that dominates the signal during its occurrence.

To increase the sign-noise distance, provision may furthermore be made to square the signal values prior to comparing them to the threshold function and the frequency number. As a result, smaller signal values are weakened relative to larger signal values, which further improves the detectability of the QRS complex.

The value of the threshold function is preferably determined adaptively from a flowing determination of the average of the band-pass filtered and squared signal values.

Details of the method according to the invention will become apparent from the ensuing description of a exemplary embodiment, taken in conjunction with the drawing.

DESCRIPTION OF THE PREFERRED EMBODIMENT

Figure 1:
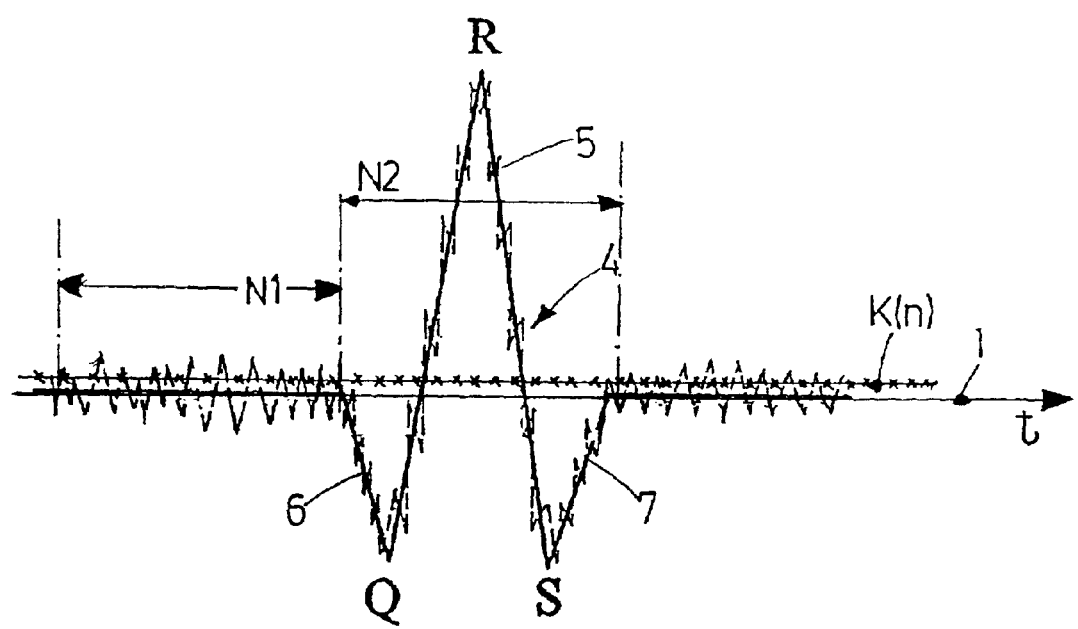
FIG. 1 is a highly schematic illustration of the signal curve of a QRS complex in an ECG signal.

As seen in FIG. 1, an idealized QRS complex consists of a relatively high-amplitude oscillation about the zero line 1 that initially guides the ECG signal 4, in the Q spike 6, away from the zero line 1 in a negative direction. Afterwards the ECG signal 4 is guided, in the R spike 5, into the positive range with a steep rise and with a subsequent steep drop back into the negative range while forming the S spike 7.

In reality, the ECG signal 4 is accompanied by a certain level of noisiness, as indicated in FIG. 1 by the dashed signal curve. If this noisy signal is sampled and converted into discrete signal values of chorological order and band-pass filtered, these signal values can be compared to the threshold function K(n) that is diagrammatically illustrated in FIG. 1 as a crisscrossed line. As can be derived clearly and by way of model from FIG. 1, the value of the ECG signal in the range outside the QRS complex mostly falls short of this threshold function K(n). In the range N1 for instance, significantly high frequencies result for signal values |x(n)| below the threshold function K(n).

In the range of the Q spike 6, the value of the ECG signal deviates very strongly from the threshold function K(n) in the positive direction. The frequency number D(n) within the segment N2 of the QRS complex 6 for this event is considerably smaller than the frequency number D(n) within the segment N1. In this regard, the frequency number D(n) may be utilized for detecting the QRS complex, the presence of which is detected when the frequency number D(n) undershoots a defined threshold $\Theta$.

Emphasis must be laid on the fact that a gist of the invention as compared to the prior art resides in that, based on the detection of the mentioned frequency number found and the comparison thereof to a defined threshold, the amplitude of the ECG signal is not checked as to whether a certain threshold is absolutely exceeded for conclusion therefrom on the QRS complex; this is the prior art way of proceeding. Rather, sort of a check is carried out as to how long the ECG signal clearly remains on a side of the threshold function that speaks in favor of the presence of a QRS complex. Only the presence of a certain duration of this condition is used as a conclusion that points to the presence of a QRS complex. Consequently, strong measuring fluctuations of only short duration are not detected as (false) QRS complexes (so-called false positive errors).

The detailed sequence of the inventive evaluation method will be explained in detail, based on FIG. 2.

The ECG signal 4 is sampled and converted into discrete signal values x(n) of chronological order. The sampling rate may be $f_t$=360 Hz, for example, i.e., the ECG signal is converted into a sequence of 360 measuring values per second. The sampled ECG signal x(n) is then subjected, on the input side, to a band-pass filtering BP that serves to remove all the signal components that do not belong to the QRS complex. This includes P and T waves as well as high-frequency noise that may originate, for example, from the bioelectrical muscle activity. The applied filter BP is linear-phase, non-recursive and has a band-pass characteristic with the pass frequencies $f_{g1}$=18 Hz and $f_{g2}$=27 Hz as well as the limiting cutoff frequencies $f_{s1}$=2 Hz and $f_{s2}$=50 Hz. The filter order is FO=26. The group delay of the band-pass filter BP accordingly corresponds to 13 sampling values and must be taken into consideration when determining the time of the occurrence of the QRS complex.

The signal values $x_f(n)$ attained in this manner are subsequently squared in a squaring step QS according to the following relation:

$$|x_f(n)|^2$$

The values $x_{fq}(n)$ thus prepared from the original signal values x(n) by a kind of computation of an absolute value are fed to a comparator complex HZ that compares these signal values to a threshold function K(n) adaptively determined therefrom. The process complex that is concerned with the determination of the threshold function K(n) is designated by AS in FIG. 2. In this complex, an appropriate value for the function coefficients K(n) is adaptively estimated from the signal values $x_{fq}(n)$. To this end, the band-pass filtered and squared signal values are recursively determined by flowing averaging by the aid of a memory factor $\lambda_k (0<\lambda_k<1)$, $$K(n)=\lambda_k K(n-1)+(1-\lambda_k)x_{fq}(n) \cdot c$$

with c being a constant.

Empirically, $\lambda_k$=0,98 and c=8 result as appropriate values.

The averaging time given by the memory factor $\lambda_k$ substantially determines the adaptation rate of this estimate, with too short as well as too long averaging signals affecting the efficiency of the signal evaluation method.

In the process complex HZ, the signal values $x_{fq}(n)$ are compared to the threshold function $K(n)$—as mentioned. In doing so, the direction is found in which the signal values $x_{fq}(n)$ deviate from the threshold function $K(n)$. A frequency number $D(n)$ within this defined segment N is determined therefrom, representing the number or frequency of events for which the signal values $x_{fq}(n)$ fall short of the threshold function. In a favorable way of calculating, $D(n)$ may also be determined recursively via $$D(n) = \lambda_D D(n-1) + (1-\lambda_D)d(n) \text{ mit } d(n) = \begin{cases} 0 \text{ für } x_{fq}(n) \geq k(n) \\ 1 \text{ für } x_{fq}(n) < k(n) \end{cases}$$

A smaller amount of the frequency number $D(n)$ indicates that the amount of the ECG signal 4 durably exceeds the threshold function $K(n)$, which is a reliable parameter for the presence of the QRS complex.

In the course of the method according to the invention, a threshold $\Theta$ still has to be determined, the undershoot of which significantly indicates the presence of a QRS complex in the defined segment of the ECG signal 4. $\Theta(n)$ is recursively computed from $D(n)$ by $$\Theta(n) = \lambda_\Theta \Theta(n-1) + (1-\lambda_\Theta)D(n)$$

with a memory factor $0 < \lambda_\Theta < 1$ being used. This memory factor for example can be selected to be $\lambda_\Theta = 0.99$. If $D(n)$ falls short of the threshold $\Theta$, a QRS complex has been detected, otherwise it has not.

Figure 2:
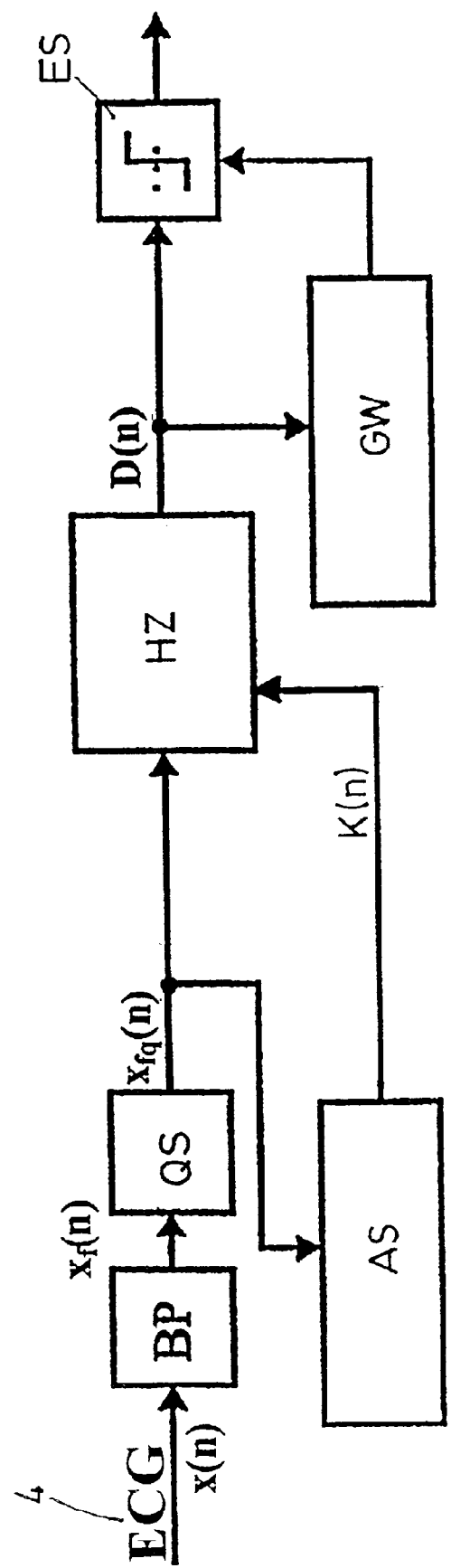
FIG. 2 is a structural diagram of the signal evaluation method according to the invention for detecting QRS complexes in ECG signals.

The job of checking whether the above requirement has been fulfilled takes place in the decision stage according to FIG. 2.

The evaluation method according to the invention can be realized by implementation based on a software-based solution in the form of a corresponding evaluation program but also by a realization based on a hardware-based solution by means of a corresponding electronic evaluation assembly.

What is claimed is:

1. A signal evaluation method for detecting QRS complexes in an electrocardiogram (ECG) signal, comprising the following steps:

sampling the ECG signal to produce consecutive sampled signal values;

converting the ECG sampled signal values into consecutive discrete signal values of chronological order;

comparing the discrete signal values to a threshold function adaptively determined from the discrete signal values;

determining a frequency number within a defined segment of the consecutive discrete signal values, the frequency number being representative of the number of discrete signal values that are below the threshold function; and comparing the determined frequency number to a defined frequency number threshold, wherein the presence of a QRS complex in the defined segment of the ECG signal is indicated when the determined frequency number is less than the frequency number threshold.

2. The signal evaluation method according to claim 1, wherein said step of converting comprises subjecting the sampled ECG signal values to a high-pass filtering.

3. The signal evaluation method according to claim 1, wherein said step of converting comprises subjecting the sampled EGG signal values to a band-pass filtering.

4. The signal evaluation method according to claim 3, wherein upper and lower limiting pass frequencies of the band-pass filter are approximately 18 Hz and approximately 27 Hz.

5. The signal evaluation method according to claim 3, wherein said step of converting further comprises generating absolute values of the filtered signal values.

6. The signal evaluation method according to claim 5, wherein said step of generating absolute values is carried out by mathematically squaring the filtered signal values.

7. The signal evaluation method according to claim 6, wherein the value of the threshold function is determined adaptively from a flowing averaging of the squared signal values for an averaging period determined by a memory factor.

8. The signal evaluation method according to claim 1, wherein the value of the threshold function is determined adaptively from a flowing averaging of the discrete signal values, for an averaging period determined by a memory factor.

9. The signal evaluation method according to claim 1, wherein the frequency number threshold is variably set as an adaptive threshold from the frequency number itself.

* * * * *